United States Patent
Yamaguchi

(10) Patent No.: US 9,103,783 B2
(45) Date of Patent: Aug. 11, 2015

(54) IONIZATION METHOD AND APPARATUS INCLUDING APPLYING CONVERGED SHOCK WAVES TO A SPRAY

(75) Inventor: Shinichi Yamaguchi, Kyoto (JP)

(73) Assignee: Shimadzu Corporation, Kyoto-Shi (JP)

(*) Notice: Subject to any disclaimer, the term of this patent is extended or adjusted under 35 U.S.C. 154(b) by 0 days.

(21) Appl. No.: 12/933,058

(22) PCT Filed: Mar. 17, 2008

(86) PCT No.: PCT/JP2008/000610
§ 371 (c)(1),
(2), (4) Date: Sep. 16, 2010

(87) PCT Pub. No.: WO2009/116114
PCT Pub. Date: Sep. 24, 2009

(65) Prior Publication Data
US 2011/0042567 A1 Feb. 24, 2011

(51) Int. Cl.
*H01J 49/00* (2006.01)
*G01N 27/62* (2006.01)
(Continued)

(52) U.S. Cl.
CPC .............. *G01N 27/62* (2013.01); *H01J 49/044* (2013.01); *H01J 49/165* (2013.01)

(58) Field of Classification Search
CPC ....................................................... H01J 49/00
USPC ........................................ 250/281, 282, 286
See application file for complete search history.

(56) References Cited

U.S. PATENT DOCUMENTS

| 5,301,659 A | * | 4/1994 | Brisson et al. | ..................... 601/4 |
| 5,373,156 A | * | 12/1994 | Franzen | ........................ 250/288 |

(Continued)

FOREIGN PATENT DOCUMENTS

| JP | 60-070062 U | 5/1985 |
| JP | 62-109346 U | 7/1987 |

(Continued)

OTHER PUBLICATIONS

International Search Report for corresponding PCT application PCT/JP2008/000610 lists the references above.

(Continued)

*Primary Examiner* — Nicole Ippolito
*Assistant Examiner* — Jason McCormack
(74) *Attorney, Agent, or Firm* — Morgan, Lewis & Bockius LLP

(57) ABSTRACT

A sample solution containing a sample component is sprayed onto an atmosphere at atmospheric approximately pressure while being applied with electric charge from the tip of a nozzle (1). A sample molecule is released as an ion in a process where charged minute liquid droplets collide with an atmospheric gas and are broken apart, and a solvent is vaporized from the respective liquid droplets. A reflectron (7) in the shape of a half-cut spheroid is arranged in such a manner that a second focal point (F2) is positioned in front of an ion-introducing portion (4) in the spray flow. A discharge electrode (8) is disposed in a position at a first focal point (F1) of the reflectron (7). When pulsed high voltage is applied to the discharge electrode (8), an electric discharge occurs, causing shock waves to be generated. The shock waves reflected on the reflectron (7) are converged on the second focal point (F2). Due to the converged shock waves, the vicinity of the second focal point (F2) rises to a high temperature, and a large pressure is also applied thereto. Therefore, vaporization of a solvent from the respective liquid droplets is further accelerated, allowing an ion to be easily generated. In addition, direct ionization can be expected. This makes it possible to improve ion generation efficiency.

14 Claims, 3 Drawing Sheets

(51) Int. Cl.
*H01J 49/04* (2006.01)
*H01J 49/16* (2006.01)

(56) References Cited

U.S. PATENT DOCUMENTS

| | | | | |
|---|---|---|---|---|
| 5,547,716 | A * | 8/1996 | Thaler | 427/577 |
| 6,485,689 | B1 * | 11/2002 | Huang et al. | 422/83 |
| 7,193,223 | B2 * | 3/2007 | Franzen | 250/425 |
| 7,259,371 | B2 * | 8/2007 | Collings et al. | 250/288 |
| 7,465,920 | B2 * | 12/2008 | Hiraoka | 250/288 |
| 7,645,983 | B2 * | 1/2010 | Hirabayashi et al. | 250/281 |
| 2002/0074491 | A1 * | 6/2002 | Fukuda | 250/288 |
| 2002/0125426 | A1 * | 9/2002 | Hirabayashi et al. | 250/288 |
| 2003/0052265 | A1 * | 3/2003 | Kato | 250/281 |
| 2004/0084616 | A1 * | 5/2004 | Hirano et al. | 250/288 |
| 2005/0001161 | A1 * | 1/2005 | Hiraoka | 250/282 |
| 2005/0045816 | A1 * | 3/2005 | Yamaguchi et al. | 250/286 |
| 2005/0199823 | A1 * | 9/2005 | Franzen | 250/425 |
| 2007/0002918 | A1 * | 1/2007 | Niemoeller et al. | 372/55 |

FOREIGN PATENT DOCUMENTS

| | | |
|---|---|---|
| JP | 05-256837 A | 10/1993 |
| JP | 08-024264 A | 1/1996 |
| JP | 2000-055880 A | 2/2000 |
| JP | 2000-106127 A | 4/2000 |
| JP | 2003-107054 A | 9/2003 |
| JP | 2004-185886 A | 2/2004 |
| JP | 2007-111682 A | 5/2007 |

OTHER PUBLICATIONS

International Preliminary Report On Patentability and Written Opinion for the counterpart International Application No. PCT/JP2008/000610.

* cited by examiner

IONIZATION METHOD AND APPARATUS INCLUDING APPLYING CONVERGED SHOCK WAVES TO A SPRAY

CROSS-REFERENCE TO THE RELATED APPLICATIONS

This application is a national stage of international application No. PCT/JP2008/000610, filed on Mar. 17, 2008, the entire contents of which are incorporated herein by reference.

TECHNICAL FIELD

The present invention relates to an ionization method and an ionization apparatus in use for generating ions to be supplied to mass spectrometry.

BACKGROUND ART

When a sample solution containing a sample component separated by a column of a liquid chromatograph is analyzed by a mass spectrometer, an atmospheric pressure ionization method (API), such as an electrospray ionization method (ESI) and an atmospheric pressure chemical ionization method (APCI), is generally used (see Patent Document 1, for example). FIG. 6(A) is a diagram showing the principle configuration of the ESI and FIG. 6(B) is a diagram showing the principle configuration of the APCI.

In the ESI the sample solution is introduced into a thin nozzle 1 having a tip to which a direct-current high-voltage of about several kilovolts is applied. The high voltage applied from a direct-current voltage source 3 imparts, to the sample solution, an electric charge having the same polarity as that of the high voltage. An electric field formed due to the potential difference between the nozzle 1 and an ion-introducing device 4 (for example, a sampling cone or a desolvation tube) arranged opposite to the nozzle 1 acts on the sample solution so that the sample solution is atomized from the tip of the nozzle 1 as it is torn apart from the nozzle 1. In order to assist the atomization of the sample solution, nebulizer gas is used which is blown out from a nebulizer gas tube 2 forming an external cylinder coaxial with the nozzle 1. The charged minute droplet sprayed out from the nozzle 1 is broken apart and micronized due to a collision with surrounding atmospheric gas and electrostatic repulsion occurring inside the minute droplet. Further, the environment is heated to an appropriate temperature, so that solvent in the minute droplet is vaporized. In a process of the micronization of the droplets, an ion derived from the sample component is released therefrom, and the generated ion is conveyed to a non-illustrated mass spectrometric device via the ion-introducing device 4.

Meanwhile, in the APCI, the sample solution is sprayed from the tip of the nozzle 1 using the nebulizer gas (such as nitrogen) brown out through the nebulizer gas tube 2. The solvent in the droplets constituting a spray flow is rapidly vaporized in the atmosphere heated to a high temperature by a heater 5. A discharge electrode 6 is arranged ahead of the spray flow. Due to corona discharge generated by the discharge electrode 6, a solvent molecule is ionized and becomes a reactant ion. The reactant ion and a sample molecule react chemically, causing the sample molecule to become an ion upon the proton addition or proton elimination, followed by being sent to the non-illustrated mass spectrometric device via the ion-introducing device 4.

As mentioned above, in the atmospheric pressure ionization method, in order to ionize the sample component in each of the sprayed droplets, a method is adopted to accelerate the vaporization of the solvent in each of the droplets by spraying high-temperature assist gas or applying heat by a heater. However, in such a conventionally adopted heating method, any drying processes cannot be performed but only a drying process by the ambient temperature at several hundred degrees Celsius at the highest. This is not necessarily enough to vaporize the solvent in a short time.

Therefore, for example, a technique has been devised in which a capillary tube having a small diameter and heated at a high temperature is used as the ion-introducing device 4 to promote the desolvation inside the capillary tube so as to enhance the production of ions (see Patent Document 2, for example). However, it is unavoidable that sample components in the droplets that do not enter the heated capillary tube will be wasted. Particularly, in the ESI, since the size of each of the droplets sprayed from the nozzle 1 is relatively large, it is not easy for the solvent in each of the droplets to vaporize, causing the ratio of the wasted sample components to be large. In order to obtain higher sensitivity in a mass spectrometer using the atmospheric pressure ionization method, it is important to allow the sample components which have conventionally been wasted to be surely ionized, and to supply them to the mass spectrometry.

Meanwhile, for the ionization of a component in a solid-state (or a caked-state) sample, a laser desorption ionization method (LDI) including, as a representative thereof, a matrix-assisted laser desorption ionization method (MALDI), is frequently used. In addition, an atmospheric pressure MALDI (AP-MALDI) is well known in which the MALDI is applied in an atmosphere at approximately atmospheric pressure. However, there is a problem that it is difficult to enhance ionization efficiency in the case of the LDI without using a matrix. In the case of the MALDI also, there are some problems, such that a matrix having an adequate laser beam absorbing quality must be chosen, and a large difference in the sensitivity may arise depending on the mixing state of the sample crystal and the matrix. In view of the above issues, development of a new ionization method instead of the LDI has been desired.

Patent Document 1

Japanese Unexamined Patent Application Publication No. 2004-185886 (paragraphs [0005] to [0007], and FIG. 6)

Patent Document 2

Japanese Unexamined Patent Application Publication No. 2003-107054

DISCLOSURE OF THE INVENTION

Problem to be Solved by the Invention

The present invention is made to solve the above problems. A first object of the present invention is to provide an ionization method and an ionization apparatus capable of promoting vaporization of a solvent in a droplet so as to perform ionization efficiently when a sample solution containing a sample component is sprayed and the ionization of the component is performed.

Furthermore, a second object of the present invention is to provide the ionization method and the ionization apparatus capable of efficiently performing the ionization of a component contained in a caked-state sample without using an auxiliary substance, such as a matrix.

Means for Solving the Problems

An ionization method relating to a first aspect of the present invention and made to solve the above problem is directed to an ionization method for ionizing a sample component for mass spectrometry, and includes the steps of spraying a sample solution containing a sample component by a spraying unit to develop a spray flow; and applying converged shock waves to the spray flow, thereby accelerating vaporization of a solvent in a minute droplet so as to promote ion generation.

Furthermore, an ionization apparatus relating to a second aspect of the present invention is directed to an apparatus for implementing the ionization method according to the first aspect, and includes: a spraying unit for spraying a sample solution containing a sample component to develop a spray flow; and a shock wave generating means for applying converged shock waves to the spray flow from the spraying unit so as to accelerate vaporization of a solvent in a minute droplet.

The ionization method relating to the first aspect of the present invention and the ionization apparatus relating to the second aspect of the present invention are useful particularly in an atmospheric pressure ionization method and an atmospheric pressure ionization apparatus where ionization is performed in an atmosphere at approximately atmospheric pressure. Specifically, the method and the apparatus can be generally used in various ionization methods including an atmospheric pressure photoionization method (APPI), in addition to the above mentioned ESI and APCI, where the sample solution is sprayed in the atmosphere at approximately atmospheric pressure.

In the ionization method relating to the first aspect of the present invention and implemented by the second aspect of the present invention, due to the action of the converged shock waves, the spray flow locally rises to a high temperature, and at the same time, is locally subjected to a high pressure. The temperature can be thousands of degrees Celsius and the pressure can be hundreds of atmospheric pressure when done in an atmosphere at normal atmospheric pressure, though it depends on the magnitude and convergence of the shock waves, gas pressure, and other factors. This makes the solvent in the droplets vaporize rapidly. In the case of the ESI, for example, since the droplets are charged, the rapid vaporization of the solvent helps the sample component to become an ion and be released. In the case of the APCI, the acceleration of the vaporization of the solvent from the droplets increases the amounts (densities) of a solvent molecule and a sample molecule in a gas phase. This activates chemical reactions, thereby improving ionization efficiency. In addition to the effect of the shock waves to the vaporization of the solvent in the droplets, it can be further expected that the shock waves directly act on the sample molecules for ionizing them.

The ionization method relating to a third aspect of the present invention and made to solve the above problem is an ionization method for ionizing a sample component for a mass spectrometry, wherein converged shock waves are applied to a sample or a preparation containing the sample component to be analyzed, thereby causing the sample component to be ionized.

The ionization apparatus relating to a fourth aspect of the present invention is an apparatus for implementing the ionization method according to the third aspect of the present invention, and includes a shock wave generating means for applying converged shock waves to the sample containing the sample component to be analyzed, so as to ionize the sample component by an effect of the shock waves.

The ionization method relating to the third aspect of the present invention and the ionization apparatus relating to the fourth aspect of the present invention are also useful particularly in the atmospheric pressure ionization method and the atmospheric pressure ionization apparatus in which the ionization is performed in the atmosphere at approximately atmospheric pressure.

In the ionization method relating to the third aspect of the present invention and implemented by the fourth aspect of the present invention, due to the converged shock waves, a surface of the sample locally rises to a high temperature, and at the same time, is locally subjected to a high pressure (vibration). The heat and the pressure cause the sample component to be vaporized from the surface of the sample, whereupon the component ionizes.

In the ionization methods relating to the first and third aspects of the present invention and the ionization apparatuses relating to the second and fourth aspects of the present invention, the generating method and the converging method of the shock waves in the shock wave generating means are not limited to any specific methods, and various methods conventionally known in the medical field or other fields can be used, including, for example, one used in gallstone destruction.

As one aspect of the present invention, the shock wave generating means can be configured so that the shock waves generated by a generating source are converged by being reflected within a half-cut spheroid. Specifically, in this configuration, the generating source can be disposed in a first focal point inside the half-cut spheroid so that the shock waves will be converged at the opposite second focal point. Accordingly, the position of the shock wave generating means may be determined in such a manner that the spray flow is blown to the position of the second focal point or the surface of the sample is disposed in the position of the second focal point. The generating source may be configured to generate the shock waves by electric discharge caused by high-power laser beams emitted from a laser beam source and converged by a lens. As another example, it may generate the shock waves by high voltage applied to a discharge electrode.

Further, as the shock wave generating means, it may be thought that the shock waves due to the vibration by multiple piezoelectric elements arranged in an inner surface of a concave surface member, and the shock waves are converged on a focal point on the concave surface, or that the shock waves are generated due to the vibration of a metallic film inside a shock tube.

Effect of the Invention

According to an ionization method relating to a first aspect of the present invention and an ionization apparatus relating to a second aspect of the present invention, ion generation efficiency can be improved and a higher amount of ions can be supplied to a mass spectrometry, compared to conventional methods and apparatuses. Therefore, detection sensitivity and detection accuracy are improved, resulting in the contribution to improvements in the qualitative and quantitative accuracy.

Also, according to the ionization method relating to the third aspect of the present invention and the ionization apparatus relating to the fourth aspect of the present invention, a component in a caked-state sample can be ionized by a method completely different from conventional methods. Since energy of the ionization directly acts on the sample component, the ionization can be performed at high efficiency without using auxiliary materials, such as a matrix used in MALDI.

BRIEF DESCRIPTION OF THE DRAWINGS

FIGS. 6(A) and 6(B) are schematic diagrams respectively showing conventional atmospheric pressure ionization apparatuses, wherein FIG. 6(A) shows an ESI type, and FIG. 6(B) shows an APCI type.

EXPLANATION OF NUMERALS

1 ... Nozzle
2 ... Nebulizer Gas Tube
3 ... Direct Current Voltage Source
4 ... Ion-Introducing Device (Sampling Cone)
5 ... Heater
6 ... Discharge Electrode
7 ... Reflector
8 ... Discharge Electrode
9 ... Discharge Source
30 ... Stage
31 ... Sample
32 ... Capillary Tube
33 ... Direct Current Source
40 ... Laser Beam Source
41 ... Lens

BEST MODES FOR CARRYING OUT THE INVENTION

[First Embodiment]

Figure 1:
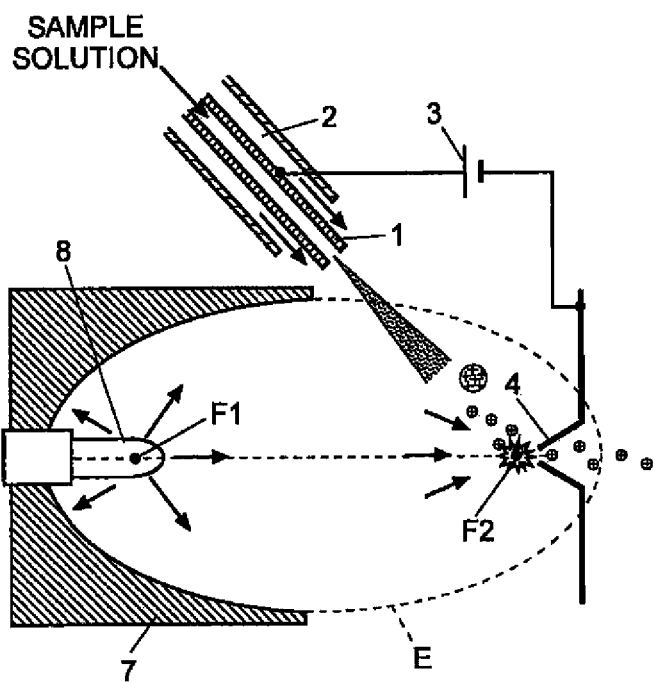
FIG. 1 is a schematic configuration diagram showing an ionization apparatus according to an embodiment of the present invention.

An ionization apparatus according to an embodiment (a first embodiment) of the present invention is described, referring to the attached drawings. FIG. 1 is a schematic configuration diagram of the ionization apparatus according to the present embodiment, and FiG. 2 is an overall configuration diagram showing an example of a mass spectrometer using The ionization apparatus.

Figure 2:
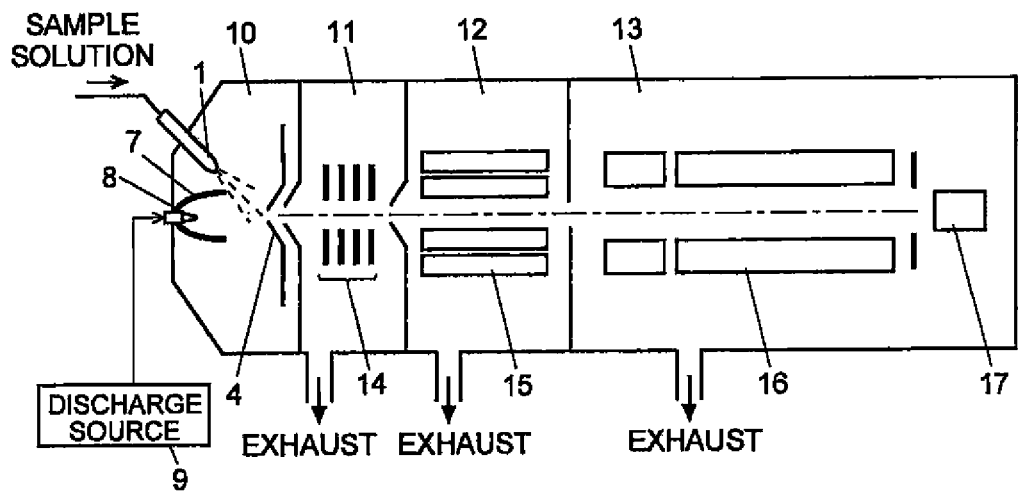
FIG. 2 is an overall configuration diagram of a mass spectrometer using the ionization apparatus shown in FIG. 1.

As shown in FIG. 2, in the mass spectrometer, two intermediate vacuum chambers 11, 12 are provided between an ionization chamber 10 maintained at an atmosphere at approximately atmospheric pressure and an analysis chamber 13 maintained at a high vacuum atmosphere. Thus, the mass spectrometer adopts a configuration of a multistage differential exhaust system enhancing the degree of vacuum gradually from the ionization chamber 10 toward the analysis chamber 13. In the ionization chamber 10, the sample components in a sample solution are ionized by an ionization apparatus which will be described later. The generated ions are conveyed to a first intermediate vacuum chamber 11 through an ion-introducing device 4.

The ions are conveyed to a later stage while they are converged by a first ion guide 14 disposed in the first intermediate vacuum chamber 11 and a second ion guide 15 disposed in a second intermediate vacuum chamber 12. Among these ions having various masses (in a precise sense, mass-to-charge ratio: m/z), an ion having a predetermined mass is selected by a quadrupole mass filter 16 disposed in the analysis chamber 13, and detected by the detector 17 upon arriving thereto. The mass of the ion capable of passing through the quadrupole mass filter 16 varies depending on the high-frequency voltage and direct current voltage applied to the quadrupole mass filter 16. Accordingly, a range of the mass of the ions arriving at the detector 17 can be scanned by varying these voltages. Therefore, a mass spectrum can be made based on the detected signal.

In the mass spectrometer of the present invention, increasing the amount of ions introduced into the quadrupole mass filter 16 improves the detection sensitivity. This can be advantageously achieved by improving the ion generation efficiency in the ionization chamber 10; in other words, in the ionization apparatus.

Figure 6:
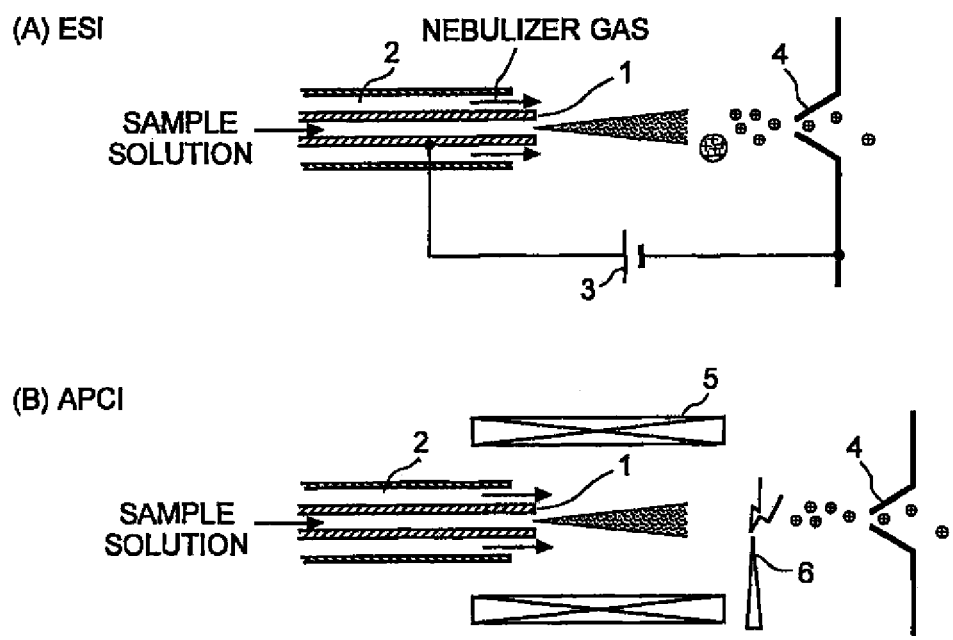

The ionization apparatus according to the first embodiment is made by applying the present invention to the electrospray ionization (ESI) apparatus shown in FIG. 6(A). The same reference numerals are allotted to the structural elements as those described with respect to FIG. 6(A). Specifically, a sample solution containing a sample component is assisted by nebulizer gas blown from a nebulizer gas tube, and is applied with a biased electric charge by the voltage applied from a direct current voltage source 3, to thereby be sprayed, as charged tiny droplets, in the atmosphere at approximately atmospheric pressure. Each of the charged tiny droplets is broken apart into minute droplets gradually by collision with the surrounding atmospheric gas or electrostatic repulsion inside each droplet. Furthermore, a solvent in the respective droplets is vaporized, and a sample molecule is released as an ion having an electric charge.

As a characteristic configuration according to the first embodiment, a reflector 7 having a reflection surface in a form of a half-cut spheroid is arranged in front of the sampling cone serving as the ion-introducing device 4. The reflection surface of the reflector 7 and a spheroid E continuing from the reflection surface have two focal points F1 and F2. A discharge electrode 8 is disposed in a position of the first focal point F1 surrounded by the reflection surface of the reflector 7. The second focal point F2 which is the other point of the two focal points is positioned immediately in front of the ion-introducing device 4 in the spray flow from the nozzle 1. The reflector 7, the discharge electrode 8, and the discharge source 9 function as the shock wave generating means in the present invention.

When a pulsed high voltage having a predetermined form is applied from the discharge source 9 to the discharge electrode 8 to cause electric discharge to occur in the discharge electrode 8, shock waves with approximately spherical wave fronts spread from the first focal point F1 to the surroundings. Except for the shock waves moving forward from the first focal point F1, in other words, moving toward the ion-introducing device 4, other shock waves are reflected on the reflector 7, and the reflected shock waves are converged on the second focal point F2. Since many of the shock waves discharged all at once from the first focal point F1 are converged on the second focal point F2, the temperature in the vicinity of the second focal point F2 becomes extremely high, and furthermore, the pressure in this region also increases.

Depending on the intensity of the shock wave generated with the discharge electrode 8, it is ideal that a temperature of several thousand degrees Celsius and pressure of several hundred atmospheres are obtained at the second focal point F2, and furthermore, the temperature in the vicinity thereof will also be higher than in the case of heating by a heater and the like. The effects of the temperature and the pressure (oscillation) further accelerate the vaporization of the solvent in the droplets, encouraging the generation of ions. The converged shocked waves act not only on the vaporization of the solvent in the droplets but also, more directly, on a sample molecule so that the sample molecule is ionized. Therefore, compared to a conventional technique, the ion generation efficiency is improved. When the same amount of the sample solution as that in the conventional technique is sprayed, greater amounts of ions can be conveyed toward a later stage through the ion-introducing device 4.

The example shown in FIG. 1 was the case where the present invention was applied to the ESI. It is also possible to apply the present invention to the APCI shown in FIG. 6(B) and the APPI to similarly enhance the ion generation efficiency.

[Second Embodiment]

Figure 3:
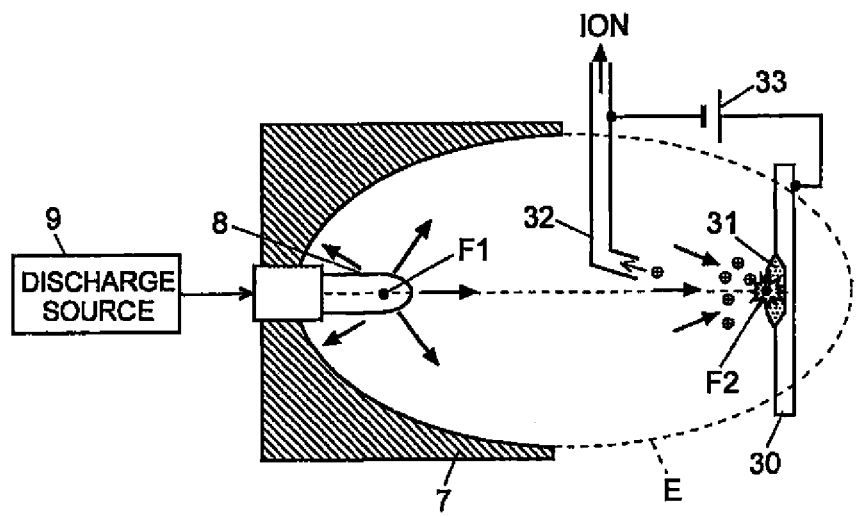
FIG. 3 is a schematic configuration diagram showing an ionization apparatus according to another embodiment of the present invention.

Next, an ionization apparatus according to another embodiment (second embodiment) of the present invention is described, referring to the attached drawings. FIG. 3 is a schematic diagram showing the ionization apparatus according to the second embodiment.

Although the same components as in the first embodiment are used in the second embodiment with respect to the shock wave generating means, specifically, the reflector 7, the discharge electrode 8 and the discharge source 9, the second focal point F2 of the spheroid E is to be positioned on a surface of a sample 31 held on a sample stage 30 in the second embodiment. The sample 31 is a solid-state sample or a caked-state sample prepared by drying a sample solution. A capillary tube 32 for collecting ions and transmitting them to the later stage is arranged as an ion-introducing device between the sample stage 30 and the discharge electrode 8.

When a pulsed high voltage having a predetermined form is applied from the discharge source 9 to the discharge electrode 8 to cause electric discharge to occur in the discharge electrode 8, shock waves with approximately spherical wave fronts spread from the first focal point F1 to the surroundings. The shock waves reflected by the reflector 7 are converged on the second focal point F2. In the second focal point F2, the sample 31 exists. Accordingly, the sample 31 locally rises to a high temperature and also undergoes additional pressure, to thereby be vaporized. This causes the ionization of the sample component in the sample 31. The generated ions are extracted from the sample 31 and suctioned into the capillary tube 32 due to the function of an electric field generated by a voltage applied from a direct current power source 33 to an area between the sample stage 30 and the capillary tube 32.

In other words, in the ionization apparatus according to the second embodiment, the converged shock waves directly act on the sample 31, causing the components in the sample 31 to be ionized. Accordingly, the matrix is not required to be used unlike in the MALDI, and only the sample 31 may be held by the sample stage 30.

Figure 4:
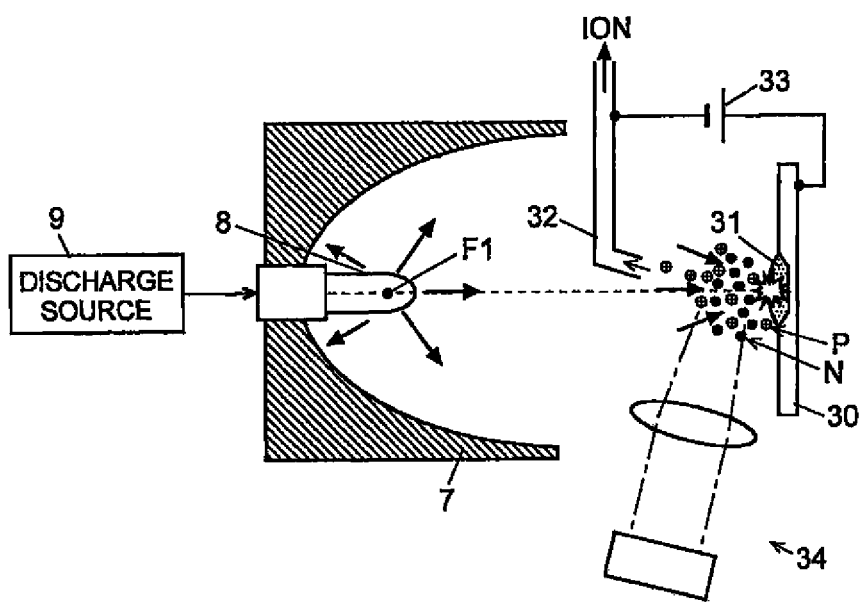
FIG. 4 is a schematic configuration diagram showing a modified embodiment of the ionization apparatus shown in FIG. 3.

FIG. 4 is a schematic configuration diagram showing a modified example of the ionization apparatus according to the second embodiment. As mentioned above, ions are released from the sample 31 by directly applying the converged shock waves to the sample 31. Many neutral particles, other than ions, derived from the sample 31 also escape from the sample 31. In other words, as diagrammatically illustrated in FIG. 4, a particle cloud in which ions P and neutral particles N are mixed together is formed around the sample 31. In the situation, the neutral particles N cannot be used for the mass spectrometry and will be eventually wasted. Therefore, the ionization apparatus according to the modified embodiment further includes a means for accelerating the ionization of the neutral particles N which have escaped from the sample 31.

In the example shown in FIG. 4, a laser beam irradiating unit 34 for irradiating the particle cloud with laser beam is provided. The laser beam excites the neutral particles N to encourage their ionization. This improves the ion generation efficiency, so that a greater amount of ions are supplied to the mass spectrometry, thereby improving analyzing sensitivity. Moreover, the ionization of neutral particles can be accelerated by, instead of the laser beam, a method of generating minute droplets charged by the same means as in the ESI and spraying the obtained minute droplets onto the particle cloud, or a method of applying an electron generated by heating a filament to the particle cloud as in the EI method, for example. When such an ionization accelerating means is additionally provided, the power of the shock waves applied to the sample 31 can be decreased and yet high ion generation efficiency can be achieved.

In the above embodiment, the electric discharge by the discharge electrode 8 is used for generating the shock waves, and the reflector 7 having the half-cut spheroid shape is used for converging the generated shock waves. However, various configurations used in, for example, the medical field (specifically, a converged shock wave generating device for crushing gall stones, for example) can be adopted as the shock wave generating means.

Figure 5:
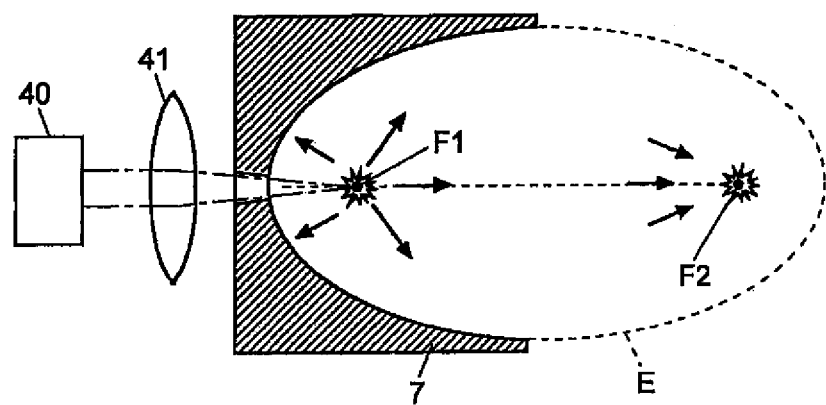
FIG. 5 is a schematic diagram showing another configuration of the shock wave generating means.

FIG. 5 is a schematic diagram showing another configuration of the shock wave generating means. In this example, a high-power laser beam emitted from a laser beam source 40 is converged by a lens 41 on the first focal point F1 of the reflector 7. This causes the electric discharge to be generated in the air, causing the shock waves to be spread spherically.

Further, a configuration may be adopted where a metallic film (a diaphragm) arranged inside a straight conduit, which is called a shock tube, is vibrated so that the shock waves are generated, and the generated shock waves are converged on a predetermined focal point by an acoustic lens. Furthermore, another configuration may be adopted where multiple piezoelectric elements are mounted on a concave reflector, and these piezoelectric elements are simultaneously driven and vibrated to generate shock waves converged on the concave reflector. Other configurations may be obviously adopted.

The above embodiments and various aspects are merely an example of the present invention, and any appropriate change, modification, or addition within the scope of the present invention is obviously involved in the scope of the claims of the present application.

The invention claimed is:

1. An ionization method for ionizing a sample component for mass spectrometry, comprising the steps of:
   spraying with a spraying unit a sample solution containing a sample component to develop a spray flow including a minute droplet; and
   applying converged shock waves with a shock wave generating member apart from the spraying unit for applying converged shock wave to the spray flow at a position immediately in front of an ion-introducing device in communication with a later stage, thereby accelerating vaporization of a solvent in the minute droplet so as to promote ion generation, wherein the shock wave generating member comprises
a discharge source;
a discharge electrode connected to the discharge source, for generating electric discharge to produce shock waves; and
a reflector for reflecting and converging the shock waves produced by the discharge electrode, where the shock waves are converged at the position immediately in front of the ion-introducing device.

2. An ionization apparatus for ionizing a sample component for mass spectrometry, comprising:
a spraying unit for spraying a sample solution containing a sample component to develop a spray flow including a minute droplet;
an ion introducing device in communication with a later stage; and
a shock wave generating member for applying converged shock waves to the spray flow from the spraying unit at a position immediately in front of the ion-introducing device so as to accelerate vaporization of a solvent in the minute droplet,
wherein the shock wave generating member comprises
a discharge source;
a discharge electrode connected to the discharge source, for generating electric discharge to produce shock waves; and
a reflector for reflecting and converging the shock waves produced by the discharge electrode, where the shock waves are converged at the position immediately in front of the ion-introducing device.

3. The ionization apparatus according to claim 2, wherein the spraying unit applies an electric charge to the sample solution and sprays the charged sample solution as charged droplets.

4. An ionization method for ionizing a sample component for mass spectrometry,
generating shock waves by a shock wave generating member, wherein the shock wave generating member comprises:
a laser beam source for emitting a laser beam;
a lens for converging the emitted laser beam to produce shock waves; and
a reflector for reflecting and converging the shock waves produced by the laser beam; and
wherein the converged shock waves are applied to a minute droplet of a sample solution to be analyzed at a position immediately in front of an ion-introducing device in communication with a later stage, thereby causing the minute droplet of the sample solution to be ionized.

5. An ionization apparatus for ionizing a sample component for mass spectrometry, comprising:
an ion-introducing device in communication with a later stage;
a shock wave generating means for applying converged shock waves to a minute droplet of a sample solution to be analyzed at a position immediately in front of the ion-introducing device,
wherein the shock wave generating member comprises:
a laser beam source for emitting a laser beam;
a lens for converging the emitted laser beam to produce shock waves; and
a reflector for reflecting and converging the shock waves produced by the laser beam, at a position immediately in front of the ion-introducing device; and
wherein the minute droplet of the sample solution is ionized by an effect of the shock waves.

6. The ionization method according to claim 1, wherein the ionization method is an atmospheric pressure ionization method performing ionization in an atmosphere at approximately atmospheric pressure.

7. The ionization apparatus according to claim 2, wherein the ionization apparatus is an atmospheric pressure ionization apparatus performing ionization in an atmosphere at approximately atmospheric pressure.

8. The ionization method according to claim 4, wherein the ionization method is an atmospheric pressure ionization method performing ionization in an atmosphere at approximately atmospheric pressure.

9. The ionization apparatus according to claim 5, wherein the ionization apparatus is an atmospheric pressure ionization apparatus performing ionization in an atmosphere at approximately atmospheric pressure.

10. The ionization apparatus according to claim 2, wherein the reflector is a half-cut spheroid shaped shock wave mirror having a first focal point and a second focal point, the discharge electrode being placed at the first focal point and the shock waves being converged at the second focal point.

11. The ionization apparatus according to claim 3, wherein the reflector is a half-cut spheroid shaped shock wave mirror having a first focal point and a second focal point, the discharge electrode being placed at the first focal point and the shock waves being converged at the second focal point.

12. The ionization apparatus according to claim 7, wherein the reflector is a half-cut spheroid shaped shock wave mirror having a first focal point and a second focal point, the discharge electrode being placed at the first focal point and the shock waves being converged at the second focal point.

13. The ionization apparatus according to claim 5, wherein the reflector is a half-cut spheroid shaped shock wave mirror having a first focal point and a second focal point, the laser beam being converged at the first focal point by the lens to produce the shock waves and the shock waves being converged at the second focal point by the reflector.

14. The ionization apparatus according to claim 9, wherein the reflector is a half-cut spheroid shaped shock wave mirror having a first focal point and a second focal point, the laser beam being converged at the first focal point by the lens to produce the shock waves and the shock waves being converged at the second focal point by the reflector.

* * * * *